United States Patent
Wu et al.

(10) Patent No.: US 6,812,222 B1
(45) Date of Patent: Nov. 2, 2004

(54) BIOCOMPATIBLE AQUEOUS SOLUTION FOR USE IN CONTINUOUS AMBULATORY PERITONEAL DIALYSIS

(75) Inventors: George Wu, 3 Caldy Court, North York, ON (CA), M2L 2J5; Paul Y. Tam, 3 Gerald Street, North York, ON (CA), M2L 2M4; Ian W. French, 6905 Highway 9, R.R. #1, Caledon East, ON (CA), L0N 1E0

(73) Assignees: George Wu, Mississauga (CA); Paul Y. Tam, Willowdale (CA); Ian W. French, Caledon East (CA)

( * ) Notice: Subject to any disclaimer, the term of this patent is extended or adjusted under 35 U.S.C. 154(b) by 211 days.

(21) Appl. No.: 09/593,691

(22) Filed: Sep. 15, 2000

Related U.S. Application Data

(63) Continuation of application No. 08/558,472, filed on Nov. 16, 1995, now Pat. No. 6,083,935.

(30) Foreign Application Priority Data

Aug. 11, 1995 (CA) ............................................. 2155910

(51) Int. Cl.$^7$ ...................... A61K 31/70; A61K 31/715; A61K 38/00
(52) U.S. Cl. ............................. 514/62; 514/53; 514/60; 514/19
(58) Field of Search .............................. 514/62, 60, 53, 514/19

(56) References Cited

U.S. PATENT DOCUMENTS

| | | | | |
|---|---|---|---|---|
| 4,870,061 A | * | 9/1989 | Speck | ........................... 514/62 |
| 4,879,280 A | * | 11/1989 | Seyffart et al. | ................ 514/53 |
| 4,886,789 A | | 12/1989 | Milner | |
| 4,996,296 A | * | 2/1991 | Pecht et al. | .................. 530/350 |
| 5,011,826 A | | 4/1991 | Steudle et al. | |
| 6,083,935 A | * | 7/2000 | Wu et al. | ...................... 514/62 |

FOREIGN PATENT DOCUMENTS

| | | | | |
|---|---|---|---|---|
| EP | 555087 | | 4/1992 | |
| EP | 0 555 087 A1 | * | 11/1993 | .......... A61K/37/02 |
| JP | 11-71273 A | * | 3/1999 | ......... A61K/31/195 |

OTHER PUBLICATIONS

West et al. "Textbook of Biochemistry", 1966, The Macmillan Company, New York, N.Y., 4$^{th}$ edition, p. 1324–1326.*

* cited by examiner

*Primary Examiner*—Shengjun Wang
(74) *Attorney, Agent, or Firm*—Kitt Sinden; Marcelo K. Sarkis; Ivor M. Hughes

(57) ABSTRACT

The present invention relates to a peritoneal dialysis solution comprising at least one amino sugar in an effective amount sufficient to create an osmotic pressure to effect the removal of water by diffusion from the patient's blood across the peritoneal membrane into the solution. In one embodiment the at least one amino sugar is selected from the group consisting of acetylated amino sugars, preferably N-acetylglucosamine, deacetylated amino sugars and combinations thereof.

14 Claims, No Drawings

BIOCOMPATIBLE AQUEOUS SOLUTION FOR USE IN CONTINUOUS AMBULATORY PERITONEAL DIALYSIS

This application is a continuation of application Ser. No. 08/558,472, filed Nov. 16, 1995 now U.S. Pat. No. 6,083,935, which claims the priority of CA 2155910, filed Aug. 11, 1995.

SUMMARY OF THE INVENTION

Continuous ambulatory peritoneal dialysis (CAPD) is used to treat end stage renal failure (ESRF) by introducing an osmotically active solution into the peritoneal cavity. Toxic waste products and excess fluid move from the blood into the dialysate solution by diffusion and ultrafiltration across the peritoneum. Osmotic ultrafiltration occurs as a result of the addition of hypertonic concentration of glucose to the dialysing solution, Due to the osmotic gradient between the blood and the CAPD solution the glucose draws water from the blood stream into the peritoneal cavity. The osmotic effect is transient and diminishes as the glucose is absorbed and/or metabolised.

In CAPD the dialysis solution is infused from collapsible plastic bags into the peritoneal cavity where it is retained for a period of time (referred to as the dwell time), after which it is drained and discarded. Generally, 3–5 treatments or exchanges of 1–3 liters each of CAPD solution are carried out daily, with an overnight dwell. The glucose concentration varies between 1.5 and 5% (w/v), with commercial CAPD solutions containing 1.5%, 2.5 or 4.5% glucose, with a high lactate content and various electrolytes which are present in more or less pH ysiologic concentrations. CAPD patients also lose 5–10 grams of protein into the dialysate per day. Commercial CAPD solutions typically have an osmolarity of 300–700 mOsm/L, preferably 350–450 mOsmol/L, as taught by U.S. Pat. No. 5,011,826.

Although peritoneal dialysis has some advantages over hemodialysis, including a substantial cost saving, there are several potential complications to CAPD. These include protein loss through the relatively highly permeable peritoneal membrane, absorption and metabolism of the added glucose resulting in weight gain and hyperlipidemia, which is particularly problematic in diabetic patients, who have a high incidence of ESRF (Ong-Ajyooth, L., Transp Proc 26: 2077, 1994).

An average patient absorbs about 150 grams of glucose from the dialysate per day, which for many patients is an excessive source of carbohydrate and results in hyperinsulinemia and hypertriglyceridemia in non-diabetic patients, which contributes to atherosclerotic disease. This series of events likely contributes to cardiovascular disease which is the most common cause of death among patients with ESRF.

Chronic exposure of the peritoneal membrane to the hypertonic and acidic CAPD solution (pH 5–6.2)can result in a loss of its function as an ultrafiltration membrane, leading to increased permeability of the peritoneal membrane and an increased rate of absorption of glucose from the dialysis solution and a loss of ultrafiltration capability. (Breborowicz et al Advances in Peritoneal Dialysis 8: 11, 1192 and Breborowicz et al Nephron 67: 350, 1994). Peritoneal biopsy samples from patients chronically dialysed with CAPD solutions show a typical epithelial reaction to irritation, mesothelial cell proliferation, as well as a decrease in the number of microvilli which normally line the mesothelial cell surface (Dobbie, J. W., Lloyd, J. K., Gall, C. A. In R. Khamma, K. D. et al Eds. Advances in peritoneal dialysis. Toronto. U of Toronto Press, 3, 1990: Friedlander, M. J Lab Clin Med 122: 639, 1993). A chronic inflammation of the peritoneum is also a consequence of chronic CAPD treatment, possibly related to the acidic nature of the CAPD solution (Lewis, S. & Holmes, C. Periton Dial Int 11: 14, 1991; Beelen, R. H. J. et al In Maher J. F., Winchester, J. F. Eds. Frontiers in peritoneal dialysis. New York: Field, Richj and Associates, 524, 1986; Bos, H. J. et al Nephron 59: 508, 1991), and which leads to healing (Weiczorowska, K. et al. Perit. Dial. Int. 15:81, 1995). Morphologic changes in the peritoneal structure also occur with chronic CAPD therapy, including fibrosis of the peritoneum (Chaimovitz, C., Kidney Int 45: 1226, 1994). Further, the use of the current relatively acidic and glucose hypertonic CAPD solutions results in a decrease in the function of peritoneal macrophages, again indicating a need for more physiologic and biocompatible CAPD solutions (deFijter, C. W. H. et al Clin Nephrology 39: 75, 1993).

As well, it has been shown that there is a loss of glycosaminoglycans (GAG's) from the peritoneal membrane which results in a loss of filtration efficiency. It has been suggested that the loss of GAG's from the peritoneal membrane is a result of the increased production of free radicals by activated peritoneal leukocytes (Breborowicz, A. et al Periton Dial Int 11 (Suppl): 35a, 1991) or because of a destructive action on interstitial tissue proteins (Fligiel, S. E. G. et al Amer J Pathol 115: 418, 1984). Supplementation of the dialysis fluid with the GAG chondroitin sulphate increases net ultrafiltration due to slower absorption of glucose and fluid from the peritoneal cavity (Advances in Peritoneal Dialysis 8: 11, 1992; Nephron 67: 346, 1994), possibly due to its ability to scavenge free radicals. Other GAG's, such as heparin and dermatan have also been reported to scavenge free radicals (Hiebert, L., Liu, J. M., Semin Thromb Hemost 17: 42, 1991; Fracasso, A. et al J Amer Soc Neph 5: 75p, 1994). It has also been reported that hyaluronan (formerly known as hyaluronic acid), which also scavenges free radicals, protects the peritoneum from injury resulting from CAPD treatment (Wieczorowska, K. et al Perit. Dial. Int. 15:81, 1995). Supporting this is the finding that the dialysis fluid collected overnight has a higher concentration of hyaluronan than serum. For example, Yung, S. et al (Kidney Int 46: 527, 1994) found that hyaluronan levels increased in the dialysate from ESRF patients with or without peritonitis undergoing CAPD treatment, and that the peritoneal mesothelial cells were the likely source of the hylauronan. Hyaluronan is important in the regulation of cell proliferation during healing. Hyaluronan is a polymer of repeating molecules of N-acetylglucosamine and glucuronic acid; dermatan is composed of repeating units of N-acetylglucosamine and iduronic acid, and chondroitin is made up of glucuronic acid and N-acetylgalactosamine.

Breborowicz and Oreopulos have submitted a PCT patent application (EP-555087-A1) (priority 92US-830721) for the addition of free radical scavengers such as GAG's, including hyaluronic acid degradation products, to CAPD solutions during episodes of peritonitis to prevent against peritonitis-associated inflammatory reactions.

As noted above, N-acetylglucosamine (NAG) is a component of many GAG's. NAG is formed in almost all cells from glucose through a series of biochemical reactions which include the addition of the amine group from glutamine to glucose to form glucosamine, with N-acetylglucosamine being synthesized by way of acetyl-CoA. NAG then is converted to NAG-6-phosphate (which is converted into the epimer of NAG, N-acetyl-mannosamine 6-phosphate which is converted to N-acetylneuraminic acid 9-phosphate which is incorporated into sialic acids, gangliosides and glycoproteins ), to NAG-1-phosphate (which is converted into UDP-N-acetylglucosamine (UDP-NAG) which is incorporated into GAG's such as chondroitins and glycoproteins). The UDP-NAG is also converted into GAG's such as hyaluronan and glycoproteins. Thus, NAG is the primary building block of many essential tissue components, whether they are comprised of NAG itself or related amino sugars such as N-acetylmannosamine and N-acetylgalactosamine.

It has been shown that orally administered glucosamine and N-acetylglucosamine (NAG) are absorbed and distributed throughout the body rapidly, and incorporated into tissues and presumably into the GAG's of the body. These compounds are incorporated into the GAG's of the peritoneal membrane to prevent their depletion thus maintaining the integrity of the peritoneal membrane, and preventing or at least slowing down, the loss of membrane function as an ultrafiltration membrane. Thus, the replacement of part or all of the glucose in the presently available CAPD solutions with amino sugars, especially NAG, should provide a more biocompatible peritoneal dialysis solution, while providing the necessary osmotic effect required for the removal of excess water and also removal of waste substances by solvent drag from patients with ESRF undergoing CAPD treatment. Unlike glucose, which is utilized by almost all microorganisms as a source of energy, the amino sugars are relatively less metabolized and not as likely to support microbial growth thus reducing the tendency for patients undergoing chronic CAPD treatment to develop peritonitis, a common and serious adverse event associated with CAPD treatment. Because of the rapid removal of NAG and other amino sugars from the systemic circulation by way of their incorporation into GAG's and various amino sugar containing tissue components the extent of metabolism into lipids is significantly reduced, thus reducing the risk of obesity, protein malnutriton, dyslipidemia and hypertriglyceridemia, hyperinsulinemia etc and the related adverse metabolic consequences.

In order for NAG and related amino sugars to be useful as osmotic agents in CAPD solutions they must have a high chemical purity similar to that which would be required for use in pharmaceutical, products, which means a minimum purity of 98.5%. NAG which is of this purity can be manufactured by two methods. The first is the acid digestion of crude chitin, which is a linear polymer of repeating units of NAG obtained from crab and shrimp shells and other crustaceans, followed by isolation of the deacetylation of the individual NAG units to glucosamine. The glucosamine is isolated and crystallized to a high level of purity and then is reacetylated using acetic anhydride to N-acetylglucosamine, which is precipitated and recrystallized from alcohol, such that its purity is greater than 98.5%. The second method of manufacturing NAG, and the preferred method, is to obtain NAG from dried crustacean shell or crude chitin by direct enzymatic digestion with an ensemble of enzymes including chitinase arid chitobiase, which degrades the chitin polymer of NAG into disaccharide units of chitobiase and then into monomer units of NAG directly, without having to undergo any organic synthetic step. The NAG is recrystallized from alcohol to a high degree of purity from ethanol. The enzymes required for this process are secreted into the growth media of various microorganisms, especially Serratia marcescens. Thus this method of manufacture not only provides NAG of a suitable purity for use in CAPD solutions but also permits the relatively inexpensive production of NAG as the chitin or crustacean shells can be added directly to the cell-free growth medium from a culture of S. marcescens and the NAG readily isolated from the medium after a suitable reaction period. By varying the length of the enzymatic reaction time the production of polymers of varying units of NAG can be produced, which can be further refined and isolated as specific molecular weight entities by way of separation using available chromatographic techniques, and which can be isolated, crystallized and further purified by recrystallization using methods familiar to those skilled in the methods of carbohydrate chemistry isolation and purification.

U.S. Pat. No. 5,011,826 teaches that CAPD solutions can use galactose alone or with glucose in varying ratios as the osmotically active agents, whereas U.S. Pat. No. 4,879,280 teaches that disaccharides such as lactose, saccharose, cellobiose etc can be used similarly, both together with suitable electrolyte additives. As well U.S. Pat. No. 4,879,280 also shows the use of trisaccharides, oligosaccharides and polysaccharides of a molecular weight less than 400,000 such as raffinose, starch, inulin, pectin, dextrans, hydroxyethyl starch (HES) and the like. For example, colloidal polymers of glucose of 4–250 glucose units long and with an weight average molecular weight of about 16,200 and a number average molecular weight of 5,800 has been clinically evaluated as component of CAPD solution (Kidney Int. 46: 496, 1994; U.S. Pat. No. 4,886,789). The osmolality of a 7.5% solution of this glucose polymer, called Icodextrin, was 282 mOsm/kg and had a pH of 5.3. However, neither the available scientific literature nor the available patents teach the use of polymers or oligomers of amino sugars such as N-acetylglucosamine, N-acetylmannosamine or N-acetylgalactosamine and the like as the osmotically active components of CAPD solutions, which are the subject of the present invention.

Since the effectiveness of intraperitoneal dialysis depends on the presence of a hypertonic solution and osmolarity depends on the number of molecules in solution, large molecules such as GAG's provide little of value to the osmotic effect of the CADP solution, and the dialysis solution must still contain excess glucose. Since N-acetylglucosamine and related amino sugars, as well as the other sugar and/or acidic carbohydrates making up the GAG's have molecular weights similar to that of glucose, they would be osmotically active. Therefore, the inclusion of amino sugars, particularly N-acetylglucosamine, in a CAPD solution at concentrations ranging from 0.5 to 5%, with or without the presence of glucose, will provide an effective dialysis solution while being more biocompatible with the peritoneal membrane and thus preventing or slowing down the morphologic and functional deterioration of the peritoneal membrane and extending the time over which ESRF patients may effectively use CAPD treatment. This provides several benefits, including substantial cost saving to the health care system by reducing the need for expensive hemodialysis, a lower rate of peritoneal infection for patients receiving CAPD treatment, a lesser risk of cardiovascular disease due to a reduction in the lipid changes typical of use of currently available CAPD solutions, and a better quality of life for such patients.

Currently marketed CAPD solutions have the following typical composition per 100 mL of solution. Dextrose anhydrous 1.5, 2.5 or 4.25 plus Sodium Chloride 567 mg, Sodium lactate 392 mg, Calcium Chloride dihydrate 23.9 mg and Magnesium Chloride hexahydrate 15.2 mg. On a milliequivalence basis this represents 132 mEq Na/L, 3.24 mEq Ca/L, 1.5 mEq Mg/L, 101.75 mEq Cl/L and 36 mEq lactate/L. Alternately, the solution may contain malate, acetate or succinate in place of lactate. The solution typically has an osmotic pressure of 347 mOsmol/L.

The CAPD solution of this invention is intended to provide similar electrolyte levels as currently available CAPD solutions, except that the osmotically active carbohydrate composition is different, being composed of acetylated and deacetylated amino sugars including N-acetylglucosamine, glucosamine, N-acetylgalactosamine, galactosamine, N-acetylmannosamine, mannosamine each alone, or in combination at varying concentrations or with varying concentrations of glucose, or oligomers of N-acetylglucosamine, N-acetylmannosamine, N-galactosamine, galactosamine, mannosamine, and glucosamine such that they are comprised of at least 2 carbohydrate units and not more than 12 units. The composition may be a mixture of oligomers of varying amounts of each oligomer either alone or in combination with each other. As well the CAPD solutions of this patent may contain additional osmotically active agents in varying proportions to the acetylated and deacetylated amino sugars such acidic carbohydrates which are also incorporated into the tissue glycosoaminoglycans (GAG's) such as glucuronic acid and iduronic acid.

In animal models of inflammatory bowel disease the colon becomes fribrotic, as does the peritoneum as a result of chronic intraperitoneal dialysis. The administration of a solution of NAG into the bowel of rats in which a chemically induced inflammatory bowel reaction with bowel wall thickening or fibrosis occurs, reduces in a dose dependent manner the fibrotic reaction to the inflammatory stimulus (Table 1). It is to be expected that in a similar manner NAG will prevent the development of fibrosis of the peritoneum in CAPD patients.

In addition to glucose CAPD solutions typically also contain a suitable number and quantity of electrolytes such that a more less physiologic solution is obtained. For example, lactate is included as a base substitute. Its absorption and metabolism will correct metabolic acidosis. Sodium is usually included at a concentration slightly lower to that found in plasma, or 132–137 mM/L, to promote sodium removal. Similarly, chloride is usually included in the CAPD solution at physiologic strengths of 100–110 mM/L.

The normal osmolarity of blood is approximately 280 mOsm/L, so that a CAPD solution must have a greater osmotic value than this if it to be effective as a dialysis solution, and preferably it should have an osmotic pressure of 300–700 mOsm/L, and more specifically 310–560, or in a more limited range, of 350 to 450 mOsm/L (from U.S. Pat. No. 4,879,280).

TABLE 1

COLON FIBROSIS
(AS MEASURED BY WEIGHT(gm) OF 8 cm OF COLON)

| INTRARECTAL ADMINISTRATION | MEAN ± SEM |
|---|---|
| Control (20 mg TNB* in 0.25 mL Ethanol) | 2.301 ± 0.222 |
| 25 mg NAG/kg BWt 1 hr before TNB/EtOH | 1.669 ± 0.142 |
| 50 mg NAG/kg BWt 1 hr before TNB/EtOH | 1.339 ± 0.155 |
| 100 mg NAG/kg BWt 1 hr before TNB/EtOH | 1.150 ± 0.068 |

*TNB = trinitrobenzenesulfonic acid

In experiments in which rats were dialyzed for 4 hours with Hanks Balances salt solution with either glucose or N-acetylglucosamine added at a concentration of 75 mM or 214 mM, at a pH of 7.35–7.4. The net utrafiltration was calculated as the difference between the drained volume of dialysate after 4 hours dwell time in the peritoneal cavity and the infused volume (20 mL) of the dialysis fluid. As well, the concentration of urea and creatinine in the blood and the dialysis fluid were measured. Permeability of the peritoneal membrane to urea and creatinine, expressed as the Mass Transfer Area Coefficient which was calculated according to the method of Krediet et al (Blood Purif 4: 194, 1986). The results, given in the Table below, clearly demonstrate that NAG results in a statistically significant increase in net ultrafiltration as well as peritoneal clearance of urea without increasing albumin or total protein loss into the dialysis fluid. In addition, the inclusion of NAG in the dialysate fluid stimulated the synthesis of hyaluronic acid, as shown by the more than 100% increase in amount of hyaluronic acid secreted in the dialysis fluid compared to the glucose treated rats. These in vivo experiments clearly demonstrate that NAG is a more effective osmotic agent than glucose when used for peritoneal dialysis.

| | Glucose 75 mM (N = 11) | NAG 75 mM (N = 14) | Glucose 214 mM (N = 11) | NAG 214 mM (N = 13) |
|---|---|---|---|---|
| Net Ultrafiltration (mL/4 hrs) | −0.44 ± 2.0 | −0.11 ± 1.6 | 11.45 ± 1.2 | 14.45 ± 1.6* |
| Mass Transfer Area Coef for Urea (mL/min) | 0.344 ± 0.13 | 0.287 ± 0.13 | 0.212 ± 0.07 | 0.262 ± 0.15 |
| Peritoneal Clearance of Urea (mL/min) | 18.8 ± 2.2 | 18.4 ± 2.1 | 26.9 ± 2.0 | 30.0 ± 2.2** |
| Total Protein Dialysate/Serum Ratio (%) | 4.3 ± 1.0 | 4.4 ± 0.6 | 2.8 ± 0.4 | 3.1 ± 0.5 |
| Albumin Dilaysate/Serum Ratio (%) | 4.0 ± 1.6 | 3.9 ± 1.2 | 1.6 ± 0.6 | 2.0 ± 0.9 |
| Hyaluronic Acid in Dialysate Fluid (ug/L) | 103 ± 21 | 226 ± 93* | 91 ± 31 | 217 ± 96*** |

*statistically significant ('t'—test), p < 0.001
**statistically significant ('test'—test), p < 0.01
***statistically significant, P < 0.002

The stimulation of hyaluronic acid by N-acetylglucosamine was confirmed in tissue culture of human mesothelial cells.

As many changes can be made to the embodiments of the invention without deporting from the scope of the invention, it is intended that all material herein be interpreted as illustrative of the invention and not in a limiting sense.

The embodiments of the invention in which and exclusive property or privilege is claimed are defined as follows:

1. In a peritoneal dialysis solution having at least one osmotically active agent in an effective amount sufficient to create an osmotic pressure to effect the removal of water from a patient's blood across the peritoneal membrane of the patient into the solution, the improvement comprises at least one amino sugar at a concentration of about 0.5% to about 5.0% (w/v) as the at least one osmotically active agent wherein said solution has an osmolarity of greater than about 280 mOsm/L.

2. The solution of claim 1 wherein the at least one amino sugar is present as a monomer or as an oligomer of 2 to 12 carbohydrate units.

3. The solution of claim 2 wherein the at least one amino sugar is selected from the group consisting of at least one acetylated amino sugar, at least one deacetylated amino sugar and combinations thereof.

4. The solution of claim 3 wherein the at least one acetylated amino sugar is selected from the group consisting of N-acetylglucosamine, N-acetylgalactosamine, N-acetylmannosamine and combinations thereof and the at least one deacetylated amino sugar is selected from the group consisting of glucosamine, galactosamine, mannosamine and combinations thereof.

5. The solution of claim 4 wherein the at least one acetylated amino sugar is N-acetylglucosamine.

6. The solution of claim 5 further comprising at least one electrolyte in an effective amount sufficient to effect the removal of solutes by diffusion from the patient's blood across the peritoneal membrane into the solution.

7. The solution of claim 6 wherein the at least one electrolyte is selected from the group consisting of sodium, calcium, chloride, magnesium, lactate, malate, acetate, succinate, and combinations thereof.

8. The solution of claim 7 further comprising at least one additional agent selected from the group consisting of glucose, iduronic acid, glucuronic acid and combinations thereof.

9. The solution of claim 8 wherein the at least one amino sugar together with the at least one additional agent is present at a concentration of about 0.5% to about 5.0% (w/v).

10. The solution of claim 9 wherein
    (a) the pH is in the range of about 5.0 to about 7.4;
    (b) the osmolarity is in the range of about 300 to about 700 mOsm/L;
    (c) sodium is present at a concentration in the range of about 115 to about 140 mEquiv/L;
    (d) calcium is present at a concentration in the range of about 0.6 to about 5.0 mEquiv/L;
    (e) chloride is present at a concentration in the range of about 100 to about 145 mEquiv/L;
    (f) magnesium is present at a concentration in the range of about 0 to about 2.0 mEquiv/L; and
    (g) lactate, malate, acetate or succinate is present at a concentration in the range of about 30 to about 45 mEquiv/L.

11. A method of performing peritoneal dialysis, said method comprising the introduction of a peritoneal dialysis solution according to claim 1, 2, 3, 4, 5, 6, 7, 8, 9 or 10 into the peritoneal cavity of a patient.

12. A method of reducing at least one complication associated with peritoneal dialysis, said method comprising the introduction of a peritoneal dialysis solution according to claim 1, 2, 3, 4, 5, 6, 7, 8, 9 or 10 into the peritoneal cavity of a patient.

13. The method of claim 12 wherein the at least one complication associated with peritoneal dialysis is selected from the group consisting of:
    (i) morphological and functional deterioration of the peritoneal membrane;
    (ii) preitonitis;
    (iii) adverse metabolic consequences and related cardiovascular disease;
    (iv) protein malnutrition and combinations thereof.

14. A method of treating a patient suffering from renal failure, said method comprising the introduction of a peritoneal dialysis solution according to claim 1, 2, 3, 4, 5, 6, 7, 8, 9 or 10 into the peritoneal cavity of a patient.

* * * * *